United States Patent
Hoshino et al.

(10) Patent No.: US 8,438,926 B2
(45) Date of Patent: May 14, 2013

(54) METHOD OF EVALUATING FASTENING STATE OF THREADED JOINT OF PIPES OR TUBES, METHOD FOR FASTENING THREADED JOINT OF PIPES OR TUBES, AND APPARATUS FOR EVALUATING FASTENING STATE OF THREADED JOINT OF PIPES OR TUBES

(75) Inventors: Ikuji Hoshino, Osaka (JP); Masaki Yamano, Osaka (JP); Makoto Sakamoto, Osaka (JP); Keiichi Nakamura, Osaka (JP); Jun Masubuchi, Osaka (JP); Kenta Sakai, Osaka (JP)

(73) Assignee: Nippon Steel & Sumitomo Metal Corporation, Tokyo (JP)

( * ) Notice: Subject to any disclaimer, the term of this patent is extended or adjusted under 35 U.S.C. 154(b) by 0 days.

(21) Appl. No.: 13/239,610

(22) Filed: Sep. 22, 2011

(65) Prior Publication Data
US 2012/0067127 A1    Mar. 22, 2012

Related U.S. Application Data

(63) Continuation of application No. PCT/JP2010/054624, filed on Mar. 18, 2010.

(30) Foreign Application Priority Data

Mar. 31, 2009 (JP) ................................ 2009-086411

(51) Int. Cl.
*G01N 29/24* (2006.01)
*G01N 29/07* (2006.01)
*G01N 29/09* (2006.01)

(52) U.S. Cl.
USPC ................................. 73/598; 73/600; 73/623

(58) Field of Classification Search .................... 73/597, 73/598, 599, 600, 623
See application file for complete search history.

(56) References Cited

U.S. PATENT DOCUMENTS

| | | | | |
|---|---|---|---|---|
| 6,158,285 A * | 12/2000 | Latimer et al. | ................... | 73/643 |
| 7,284,433 B2 * | 10/2007 | Ales et al. | ........................ | 73/597 |
| 8,091,425 B2 * | 1/2012 | Hoshino et al. | ................... | 73/598 |
| 8,113,055 B2 * | 2/2012 | Hoshino et al. | ................... | 73/600 |
| 2009/0114021 A1 * | 5/2009 | den Boer | ........................ | 73/596 |

FOREIGN PATENT DOCUMENTS

| | | |
|---|---|---|
| JP | 49-84294 | 8/1974 |
| JP | 57-20660 | 2/1982 |
| JP | 03-183944 | 8/1991 |

(Continued)

*Primary Examiner* — Peter Macchiarolo
*Assistant Examiner* — Rose M Miller
(74) *Attorney, Agent, or Firm* — Clark & Brody

(57) ABSTRACT

The present invention provides a method which allows simply, easily and accurately evaluating the fastening state of shoulder parts of a threaded joint for use as a joint of pipes or tubes, such as OCTG, during fastening or after fastening. The fastening state evaluation method for a threaded joint 100 of pipes or tubes according to the present invention is characterized in that it transmits ultrasonic surface waves from the internal surface of either one of the pin 1 and the box 2 toward the internal surface of the other one of the pin 1 and the box 2 through the shoulder parts 13, 23 of the pin 1 and the box 2, and on the basis of the transmitted wave intensity or the reflected wave intensity thereof, determines whether or not the fastening state of the threaded joint 100 is satisfactory.

6 Claims, 10 Drawing Sheets

FOREIGN PATENT DOCUMENTS

| | | |
|---|---|---|
| JP | 03-272456 | 12/1991 |
| JP | 04-265855 | 9/1992 |
| JP | 10-267175 | 10/1998 |
| JP | 2003-227816 | 8/2003 |
| JP | 2008-89568 | 4/2008 |
| JP | 2008089568 A * | 4/2008 |
| RU | 2310837 A * | 11/2007 |
| SU | 1420520 A * | 8/1988 |
| WO | WO 03106992 A2 * | 12/2003 |

* cited by examiner

METHOD OF EVALUATING FASTENING STATE OF THREADED JOINT OF PIPES OR TUBES, METHOD FOR FASTENING THREADED JOINT OF PIPES OR TUBES, AND APPARATUS FOR EVALUATING FASTENING STATE OF THREADED JOINT OF PIPES OR TUBES

TECHNICAL FIELD

The present invention relates to a method which allows simply, easily and accurately evaluating the fastening state of shoulder parts of a threaded joint which is used as a joint of pipes or tubes, such as OCTG (Oil Country Tubular Goods), during fastening or after fastening, a method for fastening a threaded joint of pipes or tubes using this evaluation method, and an apparatus for evaluating the fastening state of a threaded joint of pipes or tubes to implement this evaluation method.

BACKGROUND ART

Conventionally, a threaded joint is widely used as a joint for OCTG. FIG. 1 is an axial sectional view schematically showing a general configuration of a threaded joint. As shown in FIG. 1, a threaded joint 100 comprises a pin 1, and a box 2 which is fastened to the pin 1. The pin 1 has an external thread part 11, a metal seal part 12 and a shoulder part 13 on the external surface. The box 2 has an internal thread part 21, a metal seal part 22 and a shoulder part 23 that correspond to the respective parts of the pin 1 on the internal surface.

The external thread part 11 and the internal thread part 21 (hereinbelow, these are generically referred to as the "thread parts 11, 21" as appropriate) perform a function for fastening the pin 1 and the box 2 by engaging with each other. The outside diameter of the metal seal part 12 is adapted to be slightly larger than the inside diameter of the metal seal part 22 (such difference between diameters is referred to as an "interference margin"). When the pin 1 is fastened to the box 2, the interference margin causes an interfacial pressure to occur in the contact portion of both metal seal parts 12, 22, and this interfacial pressure (contact interfacial pressure) satisfactorily holds the airtightness of the threaded joint 100. The shoulder parts 13, 23 perform a function for preventing the metal seal parts 12, 22 from generating so high a contact interfacial pressure as to cause an excessive plastic deformation, and securing a sufficiently large amount of screwing-in to make the fastening of the threaded joint 100 reliable. Some threaded joints not only provide an interference margin for the metal seal parts 12, 22, but also provide an interference margin similar to that for the metal seal parts 12, 22 for the thread parts 11, 21 in order to make the engagement between the thread parts 11, 21 reliable such that they will not be easily loosened. In this case, the shoulder parts 13, 23 also perform a function for restricting the interference between the thread parts 11, 21 to within the safe region, thereby suppressing generation of excessive stresses in the box 2.

As a method for evaluating the fastening state of a threaded joint having the above configuration, a method which monitors a change in torque generated at the time of fastening a threaded joint has conventionally found widespread use (for example, referring to JP 10-267175A). FIG. 2 is an explanatory drawing illustrating the conventional method for evaluating the fastening state of a threaded joint. As shown in FIG. 2, as fastening of a threaded joint is progressed in sequence, a torque is generated, resulting from a friction resistance due to an interference between the thread parts 11, 21, and an interference between the metal seal parts 12, 22. Then with the shoulder parts 13, 23 being butted against each other, the torque is abruptly raised. Conventionally, by the operator observing such a change in torque, whether or not the fastening state of the threaded joint is satisfactory has been determined. Specifically, for example, when the torque is raised to above a predetermined threshold value, the operator determines that the shoulder parts 13, 23 have butted against each other, and considers that the fastening of the threaded joint 100 has been satisfactorily completed.

However, the conventional evaluation method shown in FIG. 2 will not measure some physical amounts individually for determining whether the thread parts 11, 21 actually interfere with each other, whether the metal seal parts 12, 22 actually interfere with each other, and whether the shoulder parts 13, 23 are actually butted against each other, respectively. It is an evaluation method which is based on an empirical criterion that the torque generation may be achieved by the tight contact of parts (by interference or butting). Certainly, a torque is generated through the tight contact of parts (by interference or butting). However, in such a case as that where the thread parts 11, 21 have had a seizure, some other factor can generate a great torque, thus simply by monitoring a change in torque, it is difficult to accurately evaluate the fastening state.

In addition, the conventional evaluation method shown in FIG. 2 is subjected to a constraint that it is required to continuously monitor the torque in the course of fastening the threaded joint (while the pin and the box being subjected to a relative movement to be fastened) (because, in a state subsequent to the fastening where the pin and the box have come to a standstill, the fastening state cannot be evaluated).

On the other hand, in some cases, whether the shoulder parts 13, 23 are butted against each other is determined by whether or not a clearance gage having a thickness of 0.1 mm can be inserted between the shoulder parts 13, 23. If the clearance gage 0.1 mm thick can be inserted between the shoulder parts 13, 23, it is determined that the shoulder parts 13, 23 are not butted against each other, which indicates the fastening state is unsatisfactory.

However, the clearance which allows insertion of a clearance gage 0.1 mm thick is as large as 0.15 mm or more, and thus there arises a problem that whether or not a clearance smaller than that is given cannot be determined.

In addition, in order to insert a clearance gage 0.1 mm thick into a clearance of 0.15 mm, it is required to position the clearance gage on a plane along this clearance and carefully insert it. Specifically, it is required to insert the clearance gage into the threaded joint from one opening end of the threaded joint (in other words, to move the clearance gage in the axial direction of the threaded joint) for positioning the clearance gage on a plane along this clearance which is followed by moving the clearance gage toward the clearance on the plane. Thus, there occurs a problem that evaluation using a clearance gage requires a lot of manpower, being time consuming.

DISCLOSURE OF THE INVENTION

The present invention has been made to solve the problems of the above-described prior art, and an object thereof is to provide a method which allows simply, easily and accurately evaluating the fastening state of shoulder parts of a threaded joint which is used as a joint of pipes or tubes, such as OCTG, during fastening or after fastening, a method for fastening a threaded joint of pipes or tubes using this evaluation method, and an apparatus for evaluating the fastening state of a threaded joint of pipes or tubes to implement this evaluation method.

To solve the object, the present inventors have vigorously examined them, and as a result, have obtained the following findings.

(1) The contact interfacial pressure between the shoulder part of the pin and the shoulder part of the box is changed according to the fastening state of these respective shoulder parts. Specifically, in a state where the shoulder part of the pin and the shoulder part of the box are tightly contacted with each other, the contact interfacial pressure is raised, as compared to that in a non-tight-contact state.

(2) The contact interfacial pressure between both shoulder parts and the transmitted wave intensity or reflected wave intensity of ultrasonic surface waves transmitted toward both shoulder parts from the internal surface of the pin or box have a correlation. Specifically, the transmitted wave intensity of ultrasonic surface waves transmitted toward both shoulder parts having a higher contact interfacial pressure is increased, while the reflected wave intensity of the same is decreased. Inversely, the transmitted wave intensity of ultrasonic surface waves transmitted toward both shoulder parts having a lower contact interfacial pressure or no contact interfacial pressure (with a clearance being given) is decreased, while the reflected wave intensity of the same is increased.

The present invention has been completed on the basis of the above-described findings of the present inventors. The present invention provides a method for evaluating the fastening state of a threaded joint of pipes or tubes, comprising a pin which has a shoulder part and in which an external thread part is formed, and a box which has a shoulder part buttable against the shoulder part of the pin and in which an internal thread part is formed, the external thread part of the pin being engaged with the internal thread part of the box, whereby the pin being fastened to the box, the method comprising: transmitting ultrasonic surface waves from the internal surface of either one of the pin and the box toward the internal surface of the other one of the pin and the box through the shoulder parts of the pin and the box; and on the basis of the transmitted wave intensity or the reflected wave intensity thereof, determining whether or not the fastening state of the threaded joint is satisfactory.

With the evaluation method according to the present invention, ultrasonic surface waves are transmitted from the internal surface of either one of the pin and the box constituting the threaded joint toward the internal surface of the other one of the pin and the box through the shoulder parts of the pin and the box. As described above, the contact interfacial pressure between the shoulder part of the pin and the shoulder part of the box is raised in a state where both shoulder parts are tightly contacted with each other. And, the transmitted wave intensity of ultrasonic surface waves transmitted toward both shoulder parts which have a higher contact interfacial pressure is increased, and the reflected wave intensity of the same is decreased, while the transmitted wave intensity of ultrasonic surface waves transmitted toward both shoulder parts having a lower contact interfacial pressure or no contact interfacial pressure (with a clearance being given) is decreased, and the reflected wave intensity of the same is increased. Therefore, on the basis of the magnitude of the transmitted wave intensity or the reflected wave intensity, the contact interfacial pressure (clearance) between both shoulder parts can be evaluated, whereby the fastening state of both shoulder parts can be determined.

The evaluation method according to the present invention is a method which, on the basis of the transmitted wave intensity or the reflected wave intensity of ultrasonic surface waves having a correlation with the contact interfacial pressure between the shoulder part of the pin and the shoulder part of the box, evaluates the contact interfacial pressure (clearance) between both shoulder parts, thereby evaluating the fastening state. On the other hand, with the above-described conventional evaluation method, it is not certain that the fastening state of which part has contributed to the change in torque, and there is a possibility that some other factors, such as a seizure, may cause a change in torque. Therefore, with the evaluation method according to the present invention, it can be expected that, as compared to the conventional evaluation method, evaluation with high accuracy can be performed.

In addition, the evaluation method according to the present invention is a method for evaluating the fastening state on the basis of the transmitted wave intensity or the reflected wave intensity of ultrasonic surface waves having a correlation with the contact interfacial pressure. Therefore, as with a conventional method, it is not an indispensable requirement to evaluate the fastening state in the course of fastening the threaded joint (while the pin and the box being subjected to a relative movement to be fastened), and it is possible to make evaluation not only in the course of fastening, but also in a state where the pin and the box have come to a standstill, which follows the fastening.

Further, the evaluation method according to the present invention requires the operator simply to transmit ultrasonic surface waves from the internal surface of either one of the pin and the box to the internal surface of the other one of the pin and the box through the shoulder parts of the pin and the box, and to detect the transmitted wave intensity or the reflected wave intensity thereof. Specifically, when the transmitted wave intensity is to be detected, a surface-wave transmission probe is placed on the internal surface of either one of the pin and the box where ultrasonic surface waves are to be transmitted, and a surface-wave reception probe is placed on the internal surface of the other one of the pin and the box where ultrasonic surface waves are to be received. Then, the ultrasonic surface waves transmitted from the surface-wave transmission probe toward the shoulder parts of the pin and the box can be received by the surface-wave reception probe to detect the intensity thereof. On the other hand, when the reflected wave intensity is to be detected, a surface wave probe for transmitting and receiving ultrasonic surface waves is placed on the internal surface of either one of the pin and the box. Then, the ultrasonic surface waves transmitted from this surface wave probe toward the shoulder parts of the pin and the box and reflected by the shoulder parts can be received by the same surface wave probe to detect the intensity thereof. Therefore, when compared to the conventional evaluation method using a clearance gage, which requires a lot of manpower, being time consuming, the evaluation method according to the present invention allows evaluation to be performed simply and easily.

To solve the object, the present invention also provides a method for fastening a threaded joint of pipes or tubes, comprising: in the course of fastening the threaded joint, using the above-described evaluation method to determine whether or not the fastening state is satisfactory; and at the stage where the result of the determination has become satisfactory, terminating the fastening of the threaded joint.

To solve the object, the present invention further provides an apparatus for evaluating the fastening state of a threaded joint of pipes or tubes, which is an apparatus for implementing the above-described evaluation method.

An evaluation apparatus, which determines whether or not the fastening state of the threaded joint is satisfactory on the basis of the transmitted wave intensity, comprises: a continuous length member which is inserted from one opening end of the threaded joint into the threaded joint; a butting member which is mounted on the insert front side of the continuous length member to be butted against the opening end; a flat plate member which is mounted to the butting member to be supported on the internal surface of the threaded joint in a state where the butting member is butted against the opening end; a surface-wave transmission probe which is mounted on the insert rear side of the continuous length member turnably in the axial direction of the threaded joint, has a convex contact surface according to the internal surface geometry of either one of the pin and the box on which it is to be placed, and transmits ultrasonic surface waves; a surface-wave reception probe which is mounted on the insert rear side of the continuous length member turnably in the axial direction of the threaded joint, has a convex contact surface according to the internal surface geometry of the other one of the pin and the box on which it is to be placed, and receives ultrasonic surface waves; and an elastic member which urges the surface-wave transmission probe and the surface-wave reception probe toward the internal surface of the pin or the box on which the respective probes are to be placed.

In the evaluation apparatus according to the present invention, depending upon the distance from one opening end (for example, the opening end of the box) to the shoulder parts of the threaded joint, the distance between the butting member and the surface-wave transmission probe, and the distance between the butting member and the surface-wave reception probe are set. Thereby, simply by inserting the continuous length member from the opening end of the threaded joint into the threaded joint, and butting the butting member against the opening end, the surface-wave transmission probe and the surface-wave reception probe can be simply and easily positioned in an appropriate location (a location with respect to the axial direction of the threaded joint). Next, in a state where the butting member is butted against the opening end, by causing the flat plate member to be supported by the internal surface of the threaded joint (by moving the continuous length member in the radial direction of the threaded joint until the end parts of the flat plate member are brought into contact with the internal surface of the threaded joint), the continuous length member is prevented from turning around the axial direction. If the continuous length member is prevented from being turned around the axial direction, turning of both surface wave probes (caused by turning of the continuous length member around the axial direction) is prevented, whereby the orientation of both surface wave probes is stabilized.

And, both surface wave probes (1) are turnably mounted with respect to the axial direction of the threaded joint, (2) have a convex contact surface according to the internal surface geometry of the pin or the box on which they are to be placed, and (3) are urged by the elastic member toward the internal surface of the pin or the box on which they are to be placed.

Therefore, it can be simply and easily realized to cause the contact surface of both surface wave probes to be brought into contact with the internal surface of the pin or the box in a stable state.

Therefore, transmission loss of ultrasonic waves at the contact surfaces of both surface wave probes is suppressed, which allows the fastening state of the shoulder parts to be accurately evaluated.

An evaluation apparatus, which determines whether or not the fastening state of the threaded joint is satisfactory on the basis of the reflected wave intensity, comprises: a continuous length member which is inserted from one opening end of the threaded joint into the threaded joint; a butting member which is mounted on the insert front side of the continuous length member to be butted against the opening end; a flat plate member which is mounted to the butting member to be supported on the internal surface of the threaded joint in a state where the butting member is butted against the opening end; a surface wave probe which is mounted on the insert rear side of the continuous length member turnably in the axial direction of the threaded joint, has a convex contact surface according to the internal surface geometry of either one of the pin and the box on which it is to be placed, and transmits and receives ultrasonic surface waves; and an elastic member which urges the surface wave probe toward the internal surface of the pin or the box on which the surface wave probe is to be placed.

This evaluation apparatus has the same configuration as that of the above-described evaluation apparatus, except that it comprises a surface wave probe for transmitting and receiving ultrasonic surface waves, and provides the same operational advantages.

With the method for evaluating the fastening state of a threaded joint of pipes or tubes according to the present invention, there can be obtained an excellent effect that the fastening state of a threaded joint which is used as a joint of pipes or tubes, such as OCTG, during fastening or after fastening can be simply, easily and accurately evaluated.

BEST MODE FOR CARRYING OUT THE INVENTION

Hereinbelow, with reference to the attached drawings, one embodiment of the method for evaluating the fastening state of a threaded joint of pipes or tubes according to the present invention will be explained.

First of all, the findings which the present inventors have obtained in the course of coming up with the present invention will be explained in detail.

Figure 1:
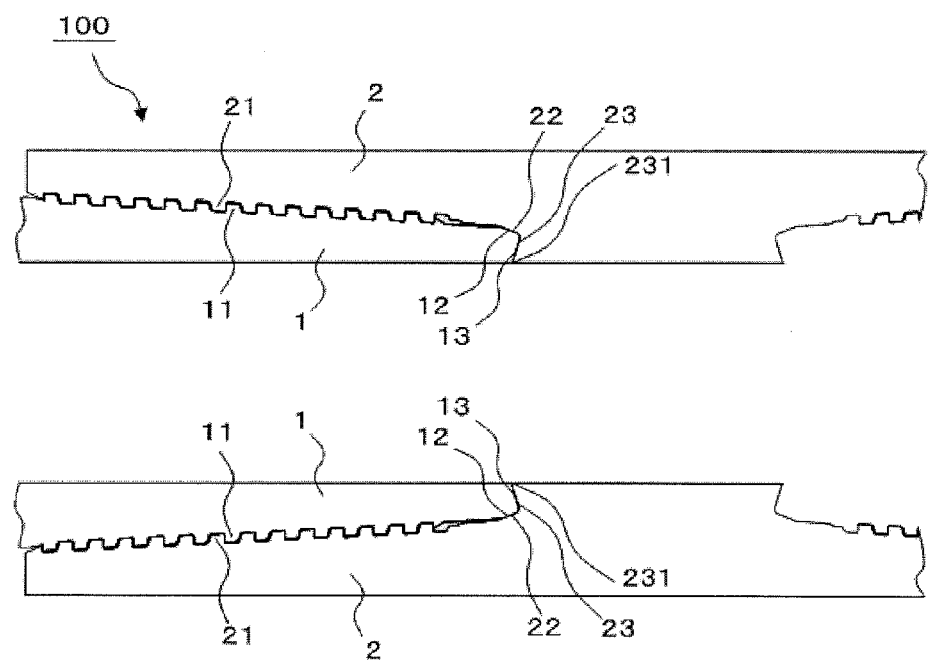
FIG. 1 is an axial sectional view schematically showing a general configuration of a threaded joint.
Figure 2:
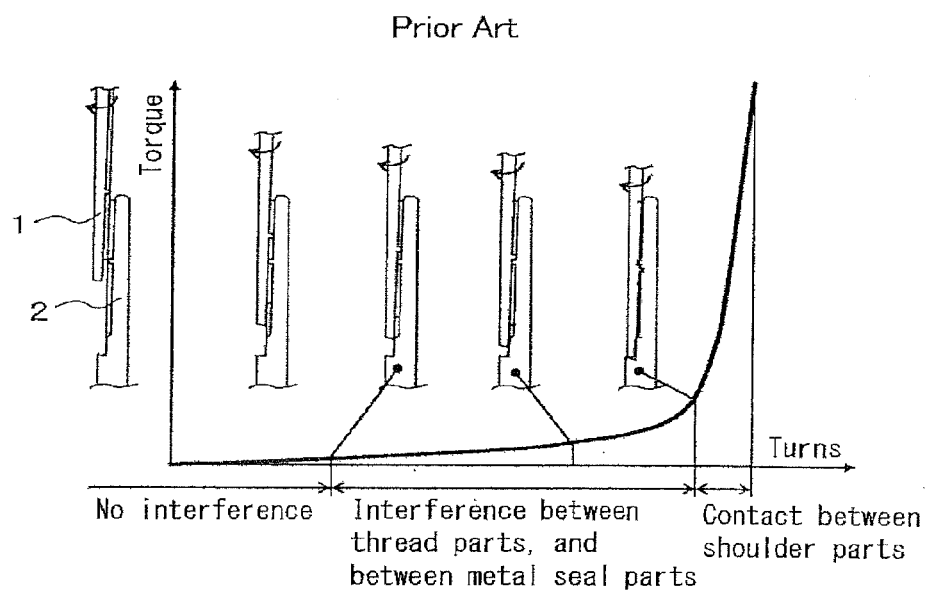
FIG. 2 is an explanatory drawing illustrating the conventional method for evaluating the fastening state of a threaded joint.

The present inventors evaluated the contact interfacial pressure between the shoulder parts 13, 23 that is generated when the threaded joint 100 shown in FIG. 1 is fastened in a state where the respective parts of the pin 1 (the external thread part 11, metal seal part 12, and shoulder part 13) and the respective parts of the box 2 (the internal thread part 21, metal seal part 22, and shoulder part 23) which constitute the threaded joint 100 are tightly contacted with each other, respectively.

Figure 3A:
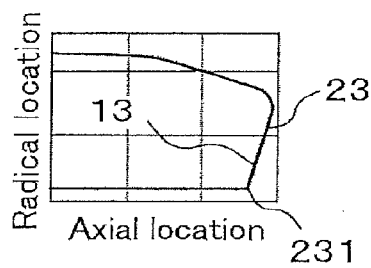
FIGS. 3A and 3B graphically show one example of the result which was calculated by a numerical computation of the contact interfacial pressure between both shoulder parts when the threaded joint is fastened in a state where the respective parts of the pin and the respective parts of the box which constitute the threaded joint are tightly contacted with each other.
Figure 3B:
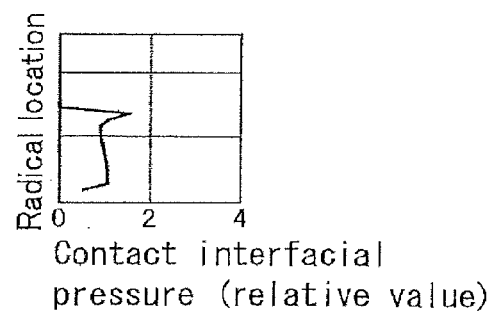

FIGS. 3A and 3B graphically show one example of the result which was calculated by a numerical computation of the contact interfacial pressure between both shoulder parts when the threaded joint is fastened in a state where the respective parts of the pin and the respective parts of the box which constitute the threaded joint are tightly contacted with each other. Specifically, the numerical computation was performed under the assumption that the minor diameter of the external thread of the external thread part 11 is adapted to be slightly larger than the major diameter of the internal thread of the internal thread part 21, the outside diameter of the metal seal part 12 is adapted to be slightly larger than the inside diameter of the metal seal part 22, and the shoulder part 13 is further screwed in toward the shoulder part 23 from a position where the shoulder part 13 has been first butted against the shoulder part 23. FIG. 3A is a partially enlarged view of a model of the threaded joint that was used for the numerical computation, and FIG. 3B is a graph illustrating the contact interfacial pressure between the shoulder parts 13, 23. In FIG. 3A and FIG. 3B, the ordinates are matched to each other.

From the result of the numerical computation that is graphically shown in FIGS. 3A and 3B, the following findings (A) to (C) have been obtained.

(A) The contact interfacial pressure between the shoulder parts 13, 23 is locally increased in a place in the vicinity of the metal seal parts 12, 22, and is also locally increased in a place in the vicinity of a corner part 231. As described above, because the outside diameter of the metal seal part 12 is adapted to be slightly larger than the inside diameter of the metal seal part 22 (in other words, an interference margin is provided), the metal seal part 12 is deformed as if it bows (is bent with the diameter being reduced). It is presumed that, with this deformation, the place in the vicinity of the metal seal parts 12, 22 of the shoulder part 13 is brought into a stronger contact with the shoulder part 23, which is a cause for the contact interfacial pressure being locally increased in the place in the vicinity of the metal seal parts 12, 22. In addition, when two machine elements are fitted to each other, the peak of the contact interfacial pressure generally appears in the vicinity of the end of the fitting portion thereof, which is presumedly a cause for the contact interfacial pressure being locally increased in the place in the vicinity of the corner part 231.

(B) When the numerical computation is performed under the assumption that the shoulder part 13 is not butted against the shoulder part 23, there appears no phenomenon in which the contact interfacial pressure is locally increased (which is not graphically shown).

(C) From the results in the above (A) and (B), it has been found that the contact interfacial pressure between the shoulder part of the pin and the shoulder part of the box is changed according to the fastening state of the shoulder parts. Specifically, in a state where the shoulder part of the pin and the shoulder part of the box are tightly contacted with each other, the contact interfacial pressure is raised, as compared to that in a non-tight-contact state. In addition, it has been found that the change in contact interfacial pressure is not uniform over the entire shoulder part, and the contact interfacial pressure is locally changed along the radial direction of the threaded joint. Specifically, in a state where the shoulder parts are tightly contacted with each other, the contact interfacial pressure is locally raised, as compared to that in a non-tight-contact state. Also in the vicinity of the corner parts of the shoulder parts, in other words, in the vicinity of the internal surfaces of the pin and the box, the contact interfacial pressure is raised.

Next, the present inventors took note of using ultrasonic surface waves to evaluate the contact interfacial pressure (clearance) between both shoulder parts. Ultrasonic surface waves are ultrasonic waves which characteristically propagate along the surface (ranging from the outermost surface to a depth as large as 1 wavelength), and although, in a portion, such as a corner, where the geometry is changed, a part thereof is reflected, further propagate along the surface in the propagating direction thereof. Therefore, if ultrasonic surface waves are transmitted from the internal surface of either one of the pin and the box toward the internal surface of the other one of the pin and the box through both shoulder parts, it can be expected that the transmitted wave intensity or the reflected wave intensity is changed according to the contact interfacial pressure (clearance) between both shoulder parts (in the vicinity of the corner part).

Figure 4A:
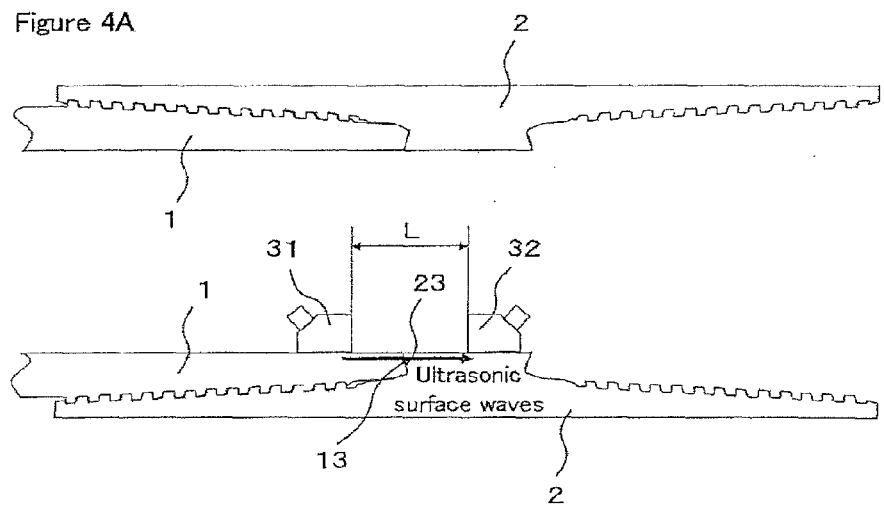
FIGS. 4A to 4C are explanatory drawings illustrating one example of the evaluation method according to the present invention.
Figure 4B:
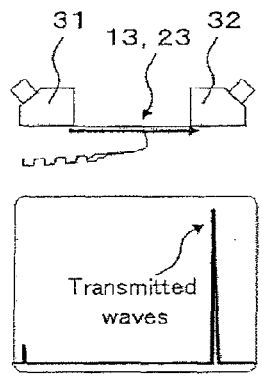
Figure 4C:
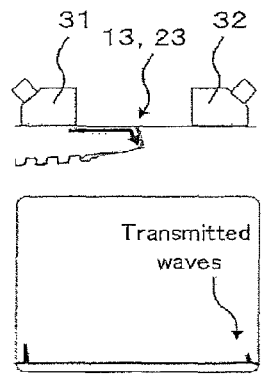

For example, consider a case where, as shown in FIG. 4A, a surface-wave transmission probe 31 is placed on the internal surface of the pin 1, and a surface-wave reception probe 32 is placed on the internal surface of the box 2 with the shoulder parts 13, 23 being sandwiched therebetween for detecting the transmitted wave intensity of ultrasonic surface waves transmitted from the surface-wave transmission probe 31 toward the shoulder parts 13, 23 with the surface-wave probe 32. It is presumed that, when the contact interfacial pressure between the shoulder parts 13, 23 is higher, the ultrasonic surface waves travel straight through the shoulder parts 13, 23 as shown in FIG. 4B, and thus the transmitted wave intensity detected with the surface-wave reception probe 32 is relatively high. On the other hand, when the contact interfacial pressure is lower or no contact interfacial pressure is generated (a clearance is given), the ultrasonic surface waves are turned around toward the external surface side in the shoulder parts 13, 23 as shown in FIG. 4C. It is presumed that the ultrasonic surface waves turned around attenuate in the course of their propagation, or the ultrasonic surface waves are reflected by the shoulder part 13, resulting in the transmitted wave intensity detected with the surface-wave reception probe 32 being decreased.

Then, the present inventors first conducted a test for evaluating the relationship of the contact interfacial pressure between both members to the transmitted wave intensity of ultrasonic surface waves transmitted toward the contact surfaces between both members. Specifically, two members M1, M2 having a rectangular sectional geometry are butted against each other with a surface-wave transmission probe 31 being placed on one member M1, and a surface-wave reception probe 32 being placed on the other member M2. As the surface-wave transmission probe 31 and the surface-wave reception probe 32, a surface wave probe having a testing frequency of 1.5 MHz and a transducer diameter of 12.7 mm was used. And, while both members M1, M2 were being subjected to a pressure in the butting direction, the transmitted wave intensity of the ultrasonic surface waves transmitted from the surface-wave transmission probe 31 toward the contact surface between the both members M1, M2 was detected with the surface-wave reception probe 32.

Figure 5:
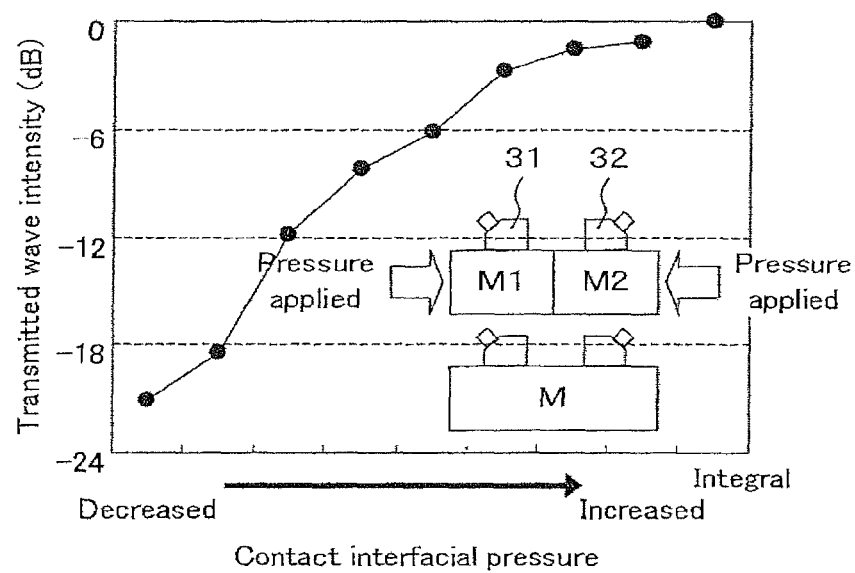
FIG. 5 is a graph illustrating one example of the relationship of the contact interfacial pressure between both members having a rectangular sectional geometry to the transmitted wave intensity of the ultrasonic surface waves.

FIG. 5 is a graph illustrating the relationship of the contact interfacial pressure between both members to the transmitted wave intensity of the ultrasonic surface waves that was obtained in the above-described evaluation test. As shown in FIG. 5, it has been found that the contact interfacial pressure between both members M1, M2 and the transmitted wave intensity of the ultrasonic surface waves have a positive correlation. And, it has been found that, when the contact interfacial pressure is sufficiently increased (when the pressure applied in the butting direction is sufficiently increased), the transmitted wave intensity of the ultrasonic surface waves for both members M1, M2 will be equivalent to that for an integral member M.

On the basis of the above result, the present inventors used the above-described method as illustrated in FIG. 4A to conduct a test on an actual threaded joint for evaluating the relationship of the contact interfacial pressure between both shoulder parts (actually the dimension of the clearance) to the transmitted wave intensity of ultrasonic surface waves transmitted toward both shoulder parts. Specifically, according to the following conditions (a) to (g), the transmitted wave intensity was detected with the surface-wave reception probe 32. The clearance between both shoulder parts was calculated on the basis of the separation distance given when the pin and the box were separated from each other, with the location where both shoulder parts were butted against each other being used as the reference.

Figure 6A:
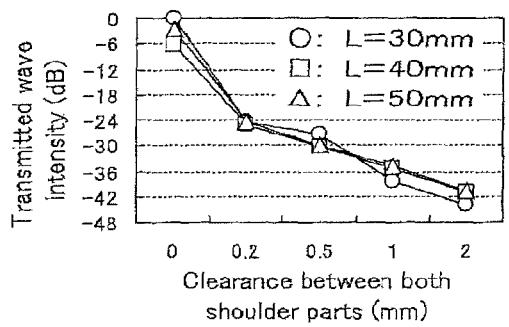
FIGS. 6A to 6D give graphs which illustrate examples of the relationship of the clearance between both shoulder parts to the transmitted wave intensity of ultrasonic surface waves that was obtained by the method shown in FIGS. 4A to 4C.
Figure 6B:
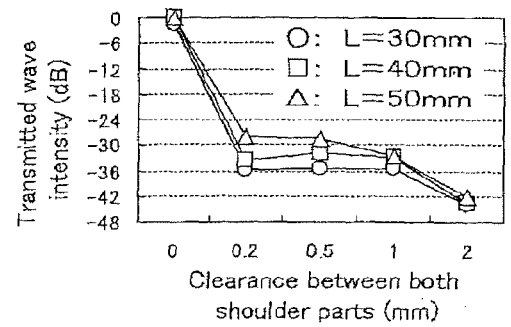
Figure 6C:
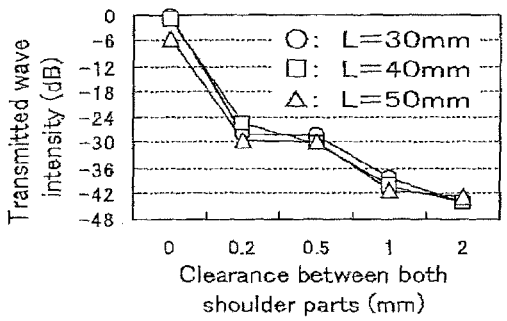
Figure 6D:
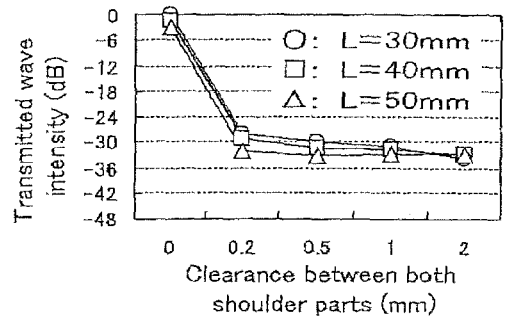

(a) Outside diameter of threaded joint (outside diameter of box): 150 mm
(b) Inside diameter of threaded joint (inside diameter of box): 100 mm
(c) Clearance between both shoulder parts: Five different clearances of 0 mm, 0.2 mm, 0.5 mm, 1.0 mm, and 2.0 mm
(d) Testing frequency for surface wave probe: Four different frequencies of 1 MHz, 1.5 MHz, 2.25 MHz, and 10 MHz
(e) Spacing between both surface wave probes (L in FIG. 4A): 30 mm, 40 mm, and 50 mm
(f) Contact medium: Lubricant, which is to be given between pin and box at the time of fastening of threaded joint; through fastening, the lubricant spilled out to the internal surfaces of the pin and the box.
(g) Ultrasonic testing apparatus: General-purpose digital ultrasonic flaw detector FIGS. 6A to 6D give graphs which illustrate the relationship of the clearance between both shoulder parts to the transmitted wave intensity of ultrasonic surface waves that was obtained by the above evaluation test. FIG. 6A illustrates the result obtained when the surface wave probes 31, 32 having a testing frequency of 1 MHz (with a transducer diameter of 12.7 mm) were used. FIG. 6B illustrates the result obtained when the surface wave probes 31, 32 having a testing frequency of 1.5 MHz (with a transducer diameter of 12.7 mm) were used. FIG. 6C illustrates the result obtained when the surface wave probes 31, 32 having a testing frequency of 2.25 MHz (with a transducer diameter of 6.4 mm) were used. FIG. 6D illustrates the result obtained when the surface wave probes 31, 32 having a testing frequency of 10 MHz (with a transducer diameter of 6.4 mm) were used.

It has been found that, as shown in FIGS. 6A to 6D, regardless of whatever testing frequency for both surface wave probes or spacing therebetween, there occurs a difference of 24 dB or larger in transmitted wave intensity of ultrasonic surface waves between the fastening state where the clearance between both shoulder parts 13, 23 is 0 mm (a satisfactory fastening state), and that where the clearance between both shoulder parts 13, 23 is 0.2 mm or larger. Therefore, it has been found that, according to the magnitude of the transmitted wave intensity of the ultrasonic surface waves, the contact interfacial pressure (clearance) between both shoulder parts 13, 23 can be evaluated, and thus whether or not the fastening state of both shoulder parts 13, 23 is satisfactory can be determined.

Although a detailed explanation is omitted here, the present inventors have also confirmed that, according to the magnitude of the reflected wave intensity of the ultrasonic surface waves, the contact interfacial pressure (clearance) between both shoulder parts 13, 23 can be evaluated, and thus whether or not the fastening state of both shoulder parts 13, 23 is satisfactory can be determined.

The present invention has been completed on the basis of the findings of the present inventors as described above, and is characterized in that ultrasonic surface waves are transmitted from the internal surface of either one of the pin 1 and the box 2 toward the internal surface of the other one of the pin 1 and the box 2 through the shoulder parts 13, 23 of the pin 1 and the box 2, and on the basis of the transmitted wave intensity or reflected wave intensity thereof, whether or not the fastening state of the threaded joint 100 is satisfactory is determined.

Hereinbelow, a specific example of the evaluation method according to the present invention (a specific example of the evaluation method using an evaluation apparatus) will be explained.

Figure 7A:
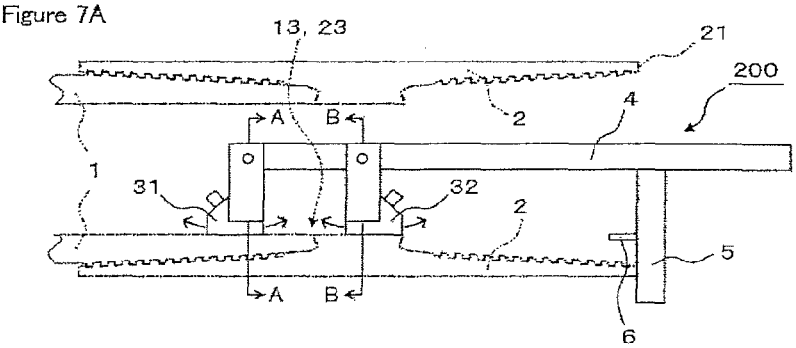
FIGS. 7A to 7D are configuration drawings which schematically show one example of the evaluation apparatus for implementing the evaluation method according to the present invention.
Figure 7B:
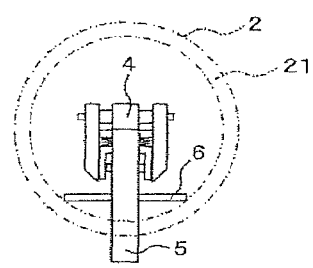
Figure 7C:
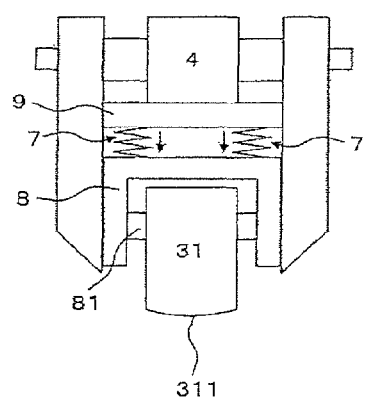
Figure 7D:
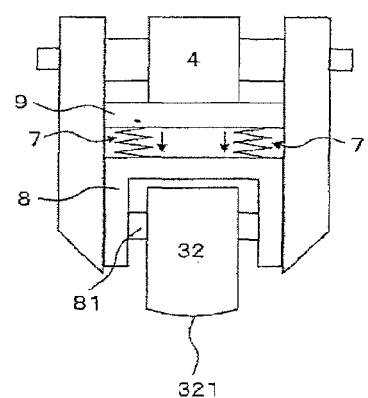

FIGS. 7A to 7D are configuration drawings which schematically show one example of the evaluation apparatus for implementing the evaluation method according to the present invention. FIG. 7A is a schematic configuration drawing of the threaded joint when viewed from the radial direction thereof; FIG. 7B is a schematic configuration drawing of the threaded joint when viewed from the axial direction thereof; FIG. 7C is an enlarged view taken in the direction of arrows A-A in FIG. 7A; and FIG. 7D is an enlarged view taken in the direction of arrows B-B in FIG. 7A.

As shown in FIGS. 7A to 7D, an evaluation apparatus 200 according to the present embodiment comprises a continuous length member 4, a butting member 5, and a flat plate member 6. The continuous length member 4 is a member which is to be inserted from one opening end of the threaded joint (an opening end 21 of the box 2 in FIGS. 7A to 7D) into the threaded joint. The butting member 5 is a member which is mounted on the insert front side of the continuous length member 4 to be butted against the opening end 21. The flat plate member 6 is a member which is mounted to the butting member 5 to be supported by the internal surface of the threaded joint (the internal surface of the box 2 in FIGS. 7A to 7D) in a state where the butting member 5 is butted against the opening end 21 (a state shown in FIG. 7A).

The evaluation apparatus 200 also comprises a surface-wave transmission probe 31 and a surface-wave reception probe 32 which are mounted on the insert rear side of the continuous length member 4. The distance between the butting member 5 and the surface-wave transmission probe 31, and the distance between the butting member 5 and the surface-wave reception probe 32 are set, depending upon the distance from the opening end 21 to the shoulder parts 13, 23. In other words, the distance from the butting member 5 to the respective surface wave probes 31, 32 is set such that, in a state where the butting member 5 is butted against the opening end 21, the surface-wave transmission probe 31 and the surface-wave reception probe 32 sandwich the shoulder parts 13, 23.

Further, the evaluation apparatus 200 comprises an elastic member 7 which urges the surface-wave transmission probe 31 and the surface-wave reception probe 32 toward the internal surfaces of the pin 1 and the box 2 on which they are to be placed, respectively. Specifically, the elastic member 7 is disposed between a basal part 9 which is mounted to the continuous length member 4, and a support member 8 which pivotally supports the surface wave probes 31, 32 as described later, urging the support member 8 toward the internal surfaces of the pin 1 and the box 2. Both ends of the elastic member 7 are fixed to the basal part 9 and the support member 8, respectively. Thereby, the surface wave probes 31, 32 pivotally supported by the support member 8 are urged toward the internal surfaces of the pin 1 and the box 2, respectively.

The surface-wave transmission probe 31 and the surface-wave reception probe 32 are mounted to the continuous length member 4 turnably in the axial direction of the threaded joint. Specifically, the surface-wave transmission probe 31 and the surface-wave reception probe 32 are pivotally supported by the support member 8 mounted to the continuous length member 4 through a shaft member 81, respectively. Thereby, the surface-wave transmission probe 31 and the surface-wave reception probe 32 are turnable in the axial direction of the threaded joint (around the shaft member 81).

The surface-wave transmission probe 31 has a convex contact surface 311 according to the internal surface geometry (nearly conformable to the internal surface geometry) of the pin 1 on which it is to be placed. Likewise, the surface-wave reception probe 32 also has a convex contact surface 321 according to the internal surface geometry (nearly conformable to the internal surface geometry) of the box 2 on which it is to be placed.

With the evaluation apparatus 200 having the above-described configuration, simply by inserting the continuous length member 4 from the opening end 21 of the threaded joint into the threaded joint, and butting the butting member 5 against the opening end 21, the surface-wave transmission probe 31 and the surface-wave reception probe 32 can be simply and easily positioned in an appropriate location (a location with respect to the axial direction of the threaded joint). Next, in a state where the butting member 5 is butted against the opening end 21, by causing the flat plate member 6 to be supported on the internal surface of the threaded joint (the internal surface of the box 2), as shown in FIG. 7B, (by moving the continuous length member 4 in the radial direction of the threaded joint until the end parts of the flat plate member 6 are brought into contact with the internal surface of the threaded joint), the continuous length member 4 is prevented from turning around the axial direction. If the continuous length member 4 is prevented from being turned around the axial direction, turning of both surface wave probes 31, 32 (caused by turning of the continuous length member 4 around the axial direction) is prevented, whereby the orientation of both surface wave probes 31, 32 is stabilized.

And, as described above, both surface wave probes 31, 32 are turnably mounted with respect to the axial direction of the threaded joint, have convex contact surfaces 311, 312 according to the internal surface geometries of the pin 1 and the box 2 on which they are to be placed, and further urged by the elastic member 7 toward the internal surfaces of the pin 1 and the box 2 on which they are to be placed. Therefore, it can be simply and easily realized to cause the contact surfaces of both surface wave probes 31, 32 to be brought into contact with the internal surfaces of the pin 1 and the box 2 in a stable state. Therefore, transmission loss of ultrasonic waves at the contact surfaces 311, 312 of both surface wave probes 31, 32 is suppressed, which allows the fastening state of the shoulder parts 13, 23 to be accurately evaluated.

Using the evaluation apparatus 200 as described above, the present inventors conducted a test for evaluating the relationship of the clearance between both shoulder parts 13, 23 to the transmitted wave intensity of ultrasonic surface waves transmitted toward both shoulder parts 13, 23. Specifically, according to the following conditions (a) to (g), the transmitted wave intensity was detected with the surface-wave reception probe 32. The clearance between both shoulder parts 13, 23 was calculated on the basis of the separation distance given when the pin 1 and the box 2 were separated from each other with the location where both shoulder parts 13, 23 were butted against each other being used as the reference.

(a) Outside diameter of threaded joint (outside diameter of box): 150 mm
(b) Inside diameter of threaded joint (inside diameter of box): 100 mm
(c) Clearance between both shoulder parts: Five different clearances of 0 mm, 0.05 mm, 0.1 mm, 0.15 mm, and 0.2 mm
(d) Testing frequency for surface wave probe: 2.25 MHz
(e) Transducer diameter of surface wave probe: 6.4 mm
(f) Spacing between both surface wave probes: 40 mm
(g) Contact medium: Lubricant, which is to be given between pin and box at the time of fastening of threaded joint; through fastening, the lubricant spilled out to the internal surfaces of the pin and the box.
(h) Ultrasonic testing apparatus: General-purpose digital ultrasonic flaw detector FIG. 8 is a graph illustrating the relationship of the clearance between both shoulder parts to the transmitted wave intensity of ultrasonic surface waves that was obtained by the above-described evaluation test.

Figure 8:
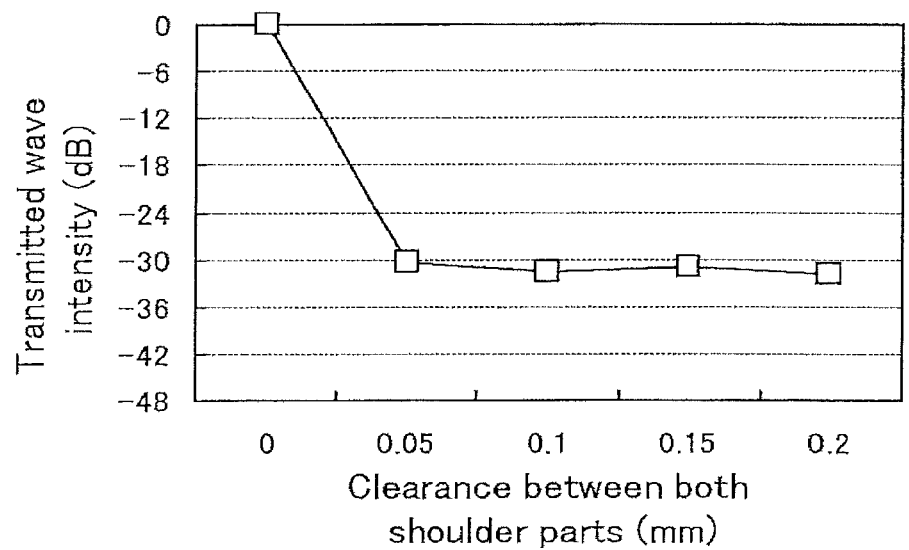
FIG. 8 is a graph illustrating one example of the relationship of the clearance between both shoulder parts to the transmitted wave intensity of ultrasonic surface waves that was obtained by using the evaluation apparatus shown in FIGS. 7A to 7D.

As can be seen from FIG. 8, there occurs a difference of 30 dB or larger in transmitted wave intensity of ultrasonic surface waves between the fastening state where the clearance between both shoulder parts 13, 23 is 0 mm (a satisfactory fastening state), and that where the clearance between both shoulder parts 13, 23 is 0.05 mm or larger. Therefore, according to the magnitude of the transmitted wave intensity of the ultrasonic surface waves, the clearance of at least 0.05 mm between both shoulder parts 13, 23 can be detected, and thus whether or not the fastening state of both shoulder parts 13, 23 is satisfactory can be determined.

Figure 9:
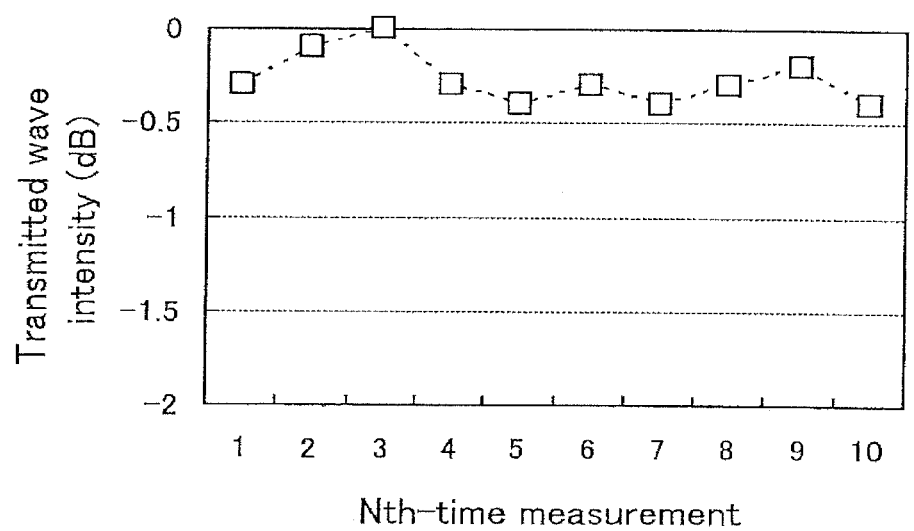
FIG. 9 is a graph illustrating one example of variations in measurement of transmitted wave intensity that was obtained by using the evaluation apparatus shown in FIGS. 7A to 7D.

FIG. 9 is a graph illustrating one example of the result of evaluation of variations in measurement of transmitted wave intensity when the clearance between both shoulder parts 13, 23 is 0 mm (when the fastening state is satisfactory) in the above-described evaluation test.

As shown in FIG. 9, by using the evaluation apparatus 200, the variation in measurement can be suppressed to as low as 0.5 dB, therefore, the fastening state of both shoulder parts 13, 23 can be accurately evaluated.

Figure 10:
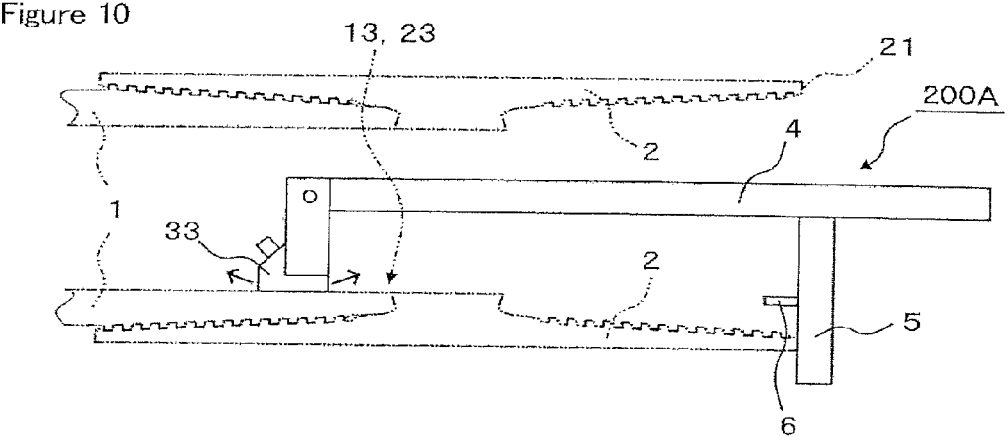
FIG. 10 is an explanatory drawing illustrating another example of the evaluation method of the present invention.

As shown in FIG. 10, an evaluation apparatus 200A, which determines whether or not the fastening state of the threaded joint is satisfactory on the basis of the reflected wave intensity, comprises: a continuous length member 4 which is inserted from one opening end 21 of the threaded joint into the threaded joint; a butting member 5 which is mounted on the insert front side of the continuous length member to be butted against the opening end; a flat plate member 6 which is mounted to the butting member 5 to be supported on the internal surface of the threaded joint in a state where the butting member 5 is butted against the opening end 21; a surface wave probe 33 which is mounted on the insert rear side of the continuous length member 4 turnably in the longitudinal axial direction of the threaded joint, has a convex contact surface according to the internal surface geometry of either one of the pin 1 and the box 2 on which it is to be placed, and transmits and receives ultrasonic surface waves; and an elastic member which urges the surface wave probe toward the internal surface of the pin or the box on which the surface wave probe 33 is to be placed.

The invention claimed is:

1. An apparatus for evaluating the fastening state of a threaded joint of pipes or tubes, the joint comprising a pin which has a shoulder part and in which an external thread part is formed, and a box which has a shoulder part buttable against the shoulder part of the pin and in which an internal thread part is formed, the external thread part of the pin being engaged with the internal thread part of the box, whereby the pin being fastened to the box, the apparatus comprising:
   a continuous length member which is inserted from one opening end of the threaded joint into the threaded joint;
   a butting member which is mounted on the insert front side of the continuous length member to be butted against the opening end;
   a flat plate member which is mounted to the butting member to be supported on the internal surface of the threaded joint in a state where the butting member is butted against the opening end;
   a surface-wave transmission probe which is mounted on the insert rear side of the continuous length member turnably in the longitudinal axial direction of the threaded joint, has a convex contact surface according to the internal surface geometry of either one of the pin and the box on which it is to be placed, and transmits ultrasonic surface waves;
   a surface-wave reception probe which is mounted on the insert rear side of the continuous length member turnably in the longitudinal axial direction of the threaded joint, has a convex contact surface according to the internal surface geometry of the other one of the pin and the box on which it is to be placed, and receives ultrasonic surface waves; and
   an elastic member which urges the surface-wave transmission probe and the surface-wave reception probe toward the internal surface of the pin or the box on which the respective probes are to be placed.

2. A method for evaluating the fastening state of a threaded joint of pipes or tubes, by using the evaluation apparatus according to claim 1, the method comprising:
   inserting the continuous length member from one opening end of the threaded joint into the threaded joint, and butting the butting member against the opening end;
   moving the continuous length member in the radial direction of the threaded joint until the end parts of the flat plate member are brought into contact with the internal surface of the threaded joint in a state where the butting member is butted against the opening end, to place the surface-wave transmission probe on the internal surface of either one of the pin and the box and to place the surface-wave reception probe on the internal surface of the other one of the pin and the box;
   transmitting ultrasonic surface waves from the surface-wave transmission probe toward the surface-wave reception probe through the shoulder parts of the pin and the box, and receiving transmitted ultrasonic surface waves by the surface-wave reception probe; and
   on the basis of the transmitted wave intensity thereof detected by the surface-wave reception probe, determining whether or not the fastening state of the threaded joint is satisfactory.

3. A method for fastening a threaded joint of pipes or tubes, comprising:
   in the course of fastening the threaded joint, using the evaluation method according to claim 2 to determine whether or not the fastening state is satisfactory; and
   at the stage where the result of the determination has become satisfactory, terminating the fastening of the threaded joint.

4. An apparatus for evaluating the fastening state of a threaded joint of pipes or tubes, the joint comprising a pin which has a shoulder part and in which an external thread part is formed, and a box which has a shoulder part buttable against the shoulder part of the pin and in which an internal thread part is formed, the external thread part of the pin being engaged with the internal thread part of the box, whereby the pin being fastened to the box, the apparatus comprising:
   a continuous length member which is inserted from one opening end of the threaded joint into the threaded joint;
   a butting member which is mounted on the insert front side of the continuous length member to be butted against the opening end;
   a flat plate member which is mounted to the butting member to be supported on the internal surface of the threaded joint in a state where the butting member is butted against the opening end;
   a surface wave probe which is mounted on the insert rear side of the continuous length member turnably in the longitudinal axial direction of the threaded joint, has a convex contact surface according to the internal surface geometry of either one of the pin and the box on which it is to be placed, and transmits and receives ultrasonic surface waves; and
   an elastic member which urges the surface wave probe toward the internal surface of the pin or the box on which the surface wave probe is to be placed.

5. A method for evaluating the fastening state of a threaded joint of pipes or tubes, by using the evaluation apparatus according to claim 4, the method comprising:
   inserting the continuous length member from one opening end of the threaded joint into the threaded joint, and butting the butting member against the opening end;
   moving the continuous length member in the radial direction of the threaded joint until the end parts of the flat plate member are brought into contact with the internal surface of the threaded joint in a state where the butting member is butted against the opening end, to place the surface-wave probe on the internal surface of either one of the pin and the box;
   transmitting ultrasonic surface waves from the surface-wave probe toward the shoulder parts of the pin and the box, and receiving reflected ultrasonic surface waves by the surface-wave probe; and
   on the basis of the reflected wave intensity thereof detected by the surface-wave probe, determining whether or not the fastening state of the threaded joint is satisfactory.

6. A method for fastening a threaded joint of pipes or tubes, comprising:
   in the course of fastening the threaded joint, using the evaluation method according to claim 5 to determine whether or not the fastening state is satisfactory; and
   at the stage where the result of the determination has become satisfactory, terminating the fastening of the threaded joint.

* * * * *